US008592175B2

(12) United States Patent
Fabrega et al.

(10) Patent No.: US 8,592,175 B2
(45) Date of Patent: Nov. 26, 2013

(54) NITROREDUCTASE ENZYMATIC SUBSTRATES

(75) Inventors: Olivier Fabrega, Newcastle upon Tyne (GB); Arthur James, Cumbria (GB); Sylvain Orenga, Neuville sur Ain (FR); John Perry, Newcastle upon Tyne (GB); Vindhya Salwatura, Newcastle Upon Tyne (GB); Stephen Stanforth, Northumberland (GB)

(73) Assignee: bioMérieux, S.A., Marcy l'Etoile (FR)

( * ) Notice: Subject to any disclaimer, the term of this patent is extended or adjusted under 35 U.S.C. 154(b) by 0 days.

(21) Appl. No.: 13/387,280

(22) PCT Filed: Jul. 29, 2010

(86) PCT No.: PCT/FR2010/051621
§ 371 (c)(1),
(2), (4) Date: Jan. 26, 2012

(87) PCT Pub. No.: WO2011/012824
PCT Pub. Date: Feb. 3, 2011

(65) Prior Publication Data
US 2012/0129204 A1 May 24, 2012

(30) Foreign Application Priority Data
Jul. 30, 2009 (FR) ...................................... 09 03756

(51) Int. Cl.
*C12Q 1/26* (2006.01)
*C07K 4/00* (2006.01)
*C07D 215/18* (2006.01)

(52) U.S. Cl.
USPC .............................. 435/25; 530/300; 546/180

(58) Field of Classification Search
None
See application file for complete search history.

(56) References Cited

U.S. PATENT DOCUMENTS

| 6,555,322 | B1 | 4/2003 | Segarini et al. |
| 2010/0221764 | A1 | 9/2010 | Fabrega et al. |

FOREIGN PATENT DOCUMENTS

| EP | 0375723 | 3/1994 |
| FR | 2916762 | 9/2010 |
| WO | WO 00/28073 | 5/2000 |
| WO | WO 2008/030120 | 3/2008 |

OTHER PUBLICATIONS

English language the Written Opinion for PCT/FR2010/051621, 2010.
English language the International Search Report for PCT/FR2010/051621, 2010.
Foley et al, "A Comparative Study of the Use of Microorganisms in the Screening of Potential Antitumor Agents", 1958, Annals of the New York Academy of Sciences, vol. 76, No. 3, pp. 413-438.
Manafi et al, "Fluorogenic and Chromogenic Substrates Used in Bacterial Diagnostics", 1991, Microb Review, vol. 55, No. 3, pp. 335-348.
McCormick et al, "Microbial Transformation of 2, 4,6-Trinitrotoluene and Other Nitroaromatic Compounds",1976, Applied and Env Microbiol,vol. 31, No. 6, pp. 949-958.
Co-pending U.S. Appl. No. 13/386,578 "Novel Peptidase Substrates" filed Jan. 23, 2012.
Co-pending U.S. Appl. No. 13/386,750 "Novel Peptidase Substrates" filed Jan. 24, 2012.
Co-pending U.S. Appl. No. 13/386,760 "Novel Peptidase Substrates" filed Jan. 24, 2012.
Co-pending U.S. Appl. No. 13/387,295 "Novel Nitroreductase Enzymatic Substrates" filed Jan. 26, 2012.
Co-pending U.S. Appl. No. 13/387,636, titled "Novel Nitroreductase Enzymatic Substrates" filed Jan. 27, 2012.

*Primary Examiner* — Robert Mondesi
*Assistant Examiner* — Md. Younus Meah

(57) ABSTRACT

The invention relates to the use of a compound having formula (I) as an enzymatic substrate for the detection of a nitroreductase activity, wherein: $W_1$, $W_2$, $W_3$ and $W_4$ are independently H, Br, Cl, F, I, alkyl, alkoxy, thiomethyl, perfluoroalkyl, nitro, cyano, carboxyl (including the esters or amides thereof) or any combination of same; n=0, 1 or 2; U is N or $N^+R$ and V is $CZ_6N$ or $N^+R$ or V is N or $N^+R$ and U is $CZ_6$, R being H, alkyl, aralkyl, aryl, alkanoic or alkylsulphonic; and $Z_1$, $Z_2$, $Z_3$, $Z_4$, $Z_5$ and $Z_6$ are independently H, Br, Cl, F, I, alkyl, aryl, alkoxy, perfluoroalkyl, nitro, cyano, carboxyl, sulphonyl, including the sulphonyl or carboxyl amides or esters thereof, and the salts of same.

7 Claims, No Drawings

NITROREDUCTASE ENZYMATIC SUBSTRATES

CROSS REFERENCE TO RELATED APPLICATIONS

This application is the national stage application under 35 USC 371 of International Application No. PCT/FR2010/051621, filed Jul. 29, 2010, which claims priority to French Patent Application No. 0903756, filed Jul. 30, 2009, the disclosures of which are hereby incorporated by reference.

The present invention relates to novel enzymatic substrates for the detection of nitroreductase activity. These substrates can be used in applications comprising a step of enzymatic reduction producing a physicochemical signal in particular in microbiology, biochemistry, immunology, molecular biology, histology and the like.

There are currently a very large number of media allowing the detection of microorganisms. This detection may be based in particular on the use of particular substrates, which are specific to an enzyme from the microorganism which it is desired to detect. In general, the synthetic substrates for enzymes are prepared in such a way that the substrate and the product of its metabolism by the target enzyme possess different physicochemical properties which make it possible to differentiate them and to evaluate if all or part of the substrate has been converted to a product by the enzyme. For example, the product of the enzymatic metabolism may be chromogenic or fluorescent. Thus, in the case of bacteria, through the choice of substrates, depending on whether there is a reaction or not, it is possible to characterize the nature of a microorganism. A nitroreductase activity may in particular be used to identify a group, a genus or a species of bacteria. It may also be used to monitor the reductive metabolism of microorganisms, for example linked to their growth or to the inhibition of this growth.

The capacity of some bacteria to reduce nitro-aromatic compounds has been known for many years. Asnis (1957) reported the isolation of a flavoprotein from extracts of *E. coli* which was capable of reducing p-nitrobenzoic acid. Since this report, the nitroaryl reductase activity has been identified in various varieties of organisms. This includes strict aerobes such as *Pseudomonas* spp. (Won et al. 1974) and *Nocardia* spp. (Villanueva 1964), strict anaerobes such as *Clostridium* spp. (Ancermaier & Simon 1983) and *Veillonella* spp. (McCormick et al. 1976), or fungi (Masuda & Ozaki 1993) and eukaryotic parasites (Douch 1975). There are a range of substrates which have been designated as being capable of being reduced by bacterial nitroaryl reductases. These are especially nitro-aromatic compounds such as p-nitrobenzoic acid, p-nitrophenol, p-nitroaniline and 2,4,6-trinitrotoluene (McCormick et al. 1976).

In general, the detection of the nitroreductase enzymatic activity is carried out by indirect methods such as monitoring of the disappearance of the substrate or of a cofactor. For example, Kitamura et al. (1983) have studied the reduction of methyl p-nitrobenzoate and of a range of other nitro-aromatic compounds with extracts of *E. coli*. However, this method is not very sensitive and is not suitable for detection in a heterogeneous medium. Mention may also be made of application WO 00/28073 which describes a fluorogenic substrate based on nitrocoumarin for the direct detection of nitroaryl reductase activities. This type of nitro-aromatic compound is capable of producing, after reduction, a very fluorescent compound which is therefore easily detectable. However, this substrate is not well suited to detection in a heterogeneous medium.

The present invention therefore proposes improving the nitroreductase substrates allowing the detection of microorganisms. Compared to existing substrates, these novel substrates are easy to synthesize, and may be used in particular in gel media for the detection of microorganisms because they produce a color which does not diffuse in the reaction medium.

In addition, the present invention contributes towards improving the state of the art in that the compounds according to the invention allow the detection of microorganisms simultaneously exhibiting a nitroreductase activity and a metabolism which causes a variation in the pH of the medium.

Before going further in the description of the invention, the definitions below are given in order to facilitate disclosure of the invention.

Enzyme substrate is understood to mean a substrate which may be modified by an enzyme into a product allowing the direct or indirect detection of a microorganism, a cell or an organelle. In the case of nitroreductase substrates, this substrate comprises in particular a nitrate functional group which is partially or completely reduced by the enzyme activity to be detected, the reduction of this nitrate functional group modifying certain physicochemical properties of the molecule, making it possible to monitor this reduction.

The substrates according to the invention are suitable for use in flow cytometry because since the product of the reduction remains mainly localized inside the cell expressing the enzyme activity, it is possible to specifically count the cells expressing this activity, or even to separate them from the remainder of the sample.

The substrates according to the invention are also well suited to use in histoenzymology because since the product of the reduction remains mainly localized at the site of the reduction, it is possible to specifically identify the cells or organelles expressing this activity within a tissue.

Because of their low toxicity, the substrates according to the invention are well suited to the monitoring of cell culture nitroreductase activity.

The substrates according to the invention are particularly well suited to use in detection and/or identification medium because they produce a color or a fluorescence which does not diffuse in the reaction medium. In the present application, the term color is used to cover a color in the visible spectrum, absorption of light, or a fluorescence, absorption at a wavelength ($\lambda_{ex}$) and emission at a higher wavelength ($\lambda_{em}$, $\lambda_{em} > \lambda_{ex}$).

The substrates of the invention may be salified, that is to say in the form of a salt such as chloride, bromide, iodide, potassium or trifluoroacetate.

The expression pH indicator is understood to mean a chemical substance whose color and/or fluorescence varies according to the pH modifications of the medium, said modifications being linked or otherwise to the metabolism of the microorganism(s) growing on said medium.

Nitroreductase is understood to mean an enzyme which can completely or partially reduce an $NO_2$ group.

Alkyl group is understood to mean a chain of saturated hydrocarbon groups, such as, in particular, a $C_1$-$C_6$ alkyl, that is to say a straight or branched alkyl having from 1 to 6 carbon atoms. By way of example, there may be mentioned methyl, ethyl, propyl, isopropyl, butyl, t-butyl, pentyl, isopentyl and hexyl.

Aryl group is understood to mean a functional group (or substituent) which is derived from an aromatic ring such as in particular an aromatic $C_6$-$C_{10}$ ring, in particular phenyl, benzyl, 1-naphthyl or 2-naphthyl.

Carboxyl group is understood to mean in particular a functional group composed of a carbon atom, linked by a double bond to a first oxygen atom, and by a single bond to a second oxygen atom, itself negatively charged or connected to a hydrogen atom. Depending on the $pK_a$ of the molecule and the pH of the medium, the carboxyl group may be in ionized form, that is to say without H linked to the second oxygen atom, which is then negatively charged.

Reaction medium is understood to mean a medium comprising all the elements necessary for the expression of a metabolism and/or for the growth of microorganisms, of a cell or of an organelle. This reaction medium may be used in flow cytometry, histoenzymology, cell culture and the like, or as a medium for detection and/or identification of microorganisms.

The reaction medium may be solid, semisolid or liquid. The expression solid medium is understood to mean for example a gel medium. Agar is the traditional gelling agent in microbiology for the culture of microorganisms, but it is possible to use gelatin or agarose. A number of preparations are commercially available, such as for example Columbia agar, trypcase-soy agar, MacConkey agar, Sabouraud agar or more generally those described in the Handbook of Microbiological Media (CRC Press).

The reaction medium may comprise one or more elements in combination, such as amino acids, peptones, carbohydrates, nucleotides, minerals, vitamins, antibiotics, surfactants, buffers, salts of phosphate, ammonium, sodium, metals.

The medium may also comprise a dye. As a guide, there may be mentioned, as dye, Evans blue, neutral red, sheep blood, horse blood, an opacifier such as titanium oxide, nitroaniline, malachite green, brilliant green and the like.

The reaction medium may be a detection and/or identification medium, that is to say a visualization medium, or a culture and visualization medium. In the first case, the microorganisms are cultured before inoculation and, in the second case, the detection and/or identification medium also constitutes the culture medium.

Biological sample is understood to mean a clinical sample, obtained from a sample of biological fluid or a food sample, obtained from any type of food or a cosmetic or pharmaceutical sample obtained from any cosmetic or pharmaceutical preparation. This sample may thus be liquid or solid and there may be mentioned, without limitation, a clinical blood, plasma, urine or stool sample, samples from the nose, throat, skin, sores, cerebrospinal fluid, a food sample of water, drinks such as milk, a fruit juice; of yoghurt, meat, eggs, vegetables, mayonnaise, cheese; of fish and the like, a food sample obtained from animal feed, such as in particular a sample obtained from bone meal. The sample may also be taken from a clinical environment, a breeding environment or a food, cosmetic or pharmaceutical production environment. The expression sample taken from an environment is understood to mean in particular a surface sample, a sample of liquid, of raw material or of product.

The expression sample is therefore understood to mean the sample proper (swab, stool, food and the like) as well as colonies of microorganisms obtained from said sample (for example after isolation on a gel culture medium, or in an enrichment broth inoculated with said sample).

For the purposes of the present invention, the term microorganism covers bacteria, in particular Gram-negative and Gram-positive bacteria, yeasts, molds, and more generally organisms that are generally unicellular and invisible to the naked eye, which may be multiplied and manipulated in the laboratory.

By way of Gram-negative bacteria, there may be mentioned bacteria of the following genera: *Pseudomonas, Escherichia, Salmonella, Shigella, Enterobacter, Klebsiella, Serratia, Proteus, Campylobacter, Haemophilus, Morganella, Vibrio, Yersinia, Acinetobacter, Branhamella, Neisseria, Burkholderia, Citrobacter, Hafnia, Edwardsiella, Aeromonas, Moraxella, Pasteurella, Providencia, Actinobacillus, Alcaligenes, Bordetella, Cedecea, Erwinia, Pantoea, Ralstonia, Stenotrophomonas, Xanthomonas* and *Legionella*.

By way of Gram-positive bacteria, there may be mentioned bacteria of the following genera: *Aerococcus, Enterococcus, Streptococcus, Staphylococcus, Bacillus, Lactobacillus, Listeria, Clostridium, Gardnerella, Kocuria, Lactococcus, Leuconostoc, Micrococcus, Falkamia, Gemella, Pediococcus, Mycobacterium* and *Corynebacterium*.

By way of yeasts, there may be mentioned yeasts of the following genera: *Candida, Cryptococcus, Saccharomyces* and *Trichosporon*.

Preferably, the microorganisms belong to the genera *Escherichia, Shigella, Salmonella, Serratia, Enterobacter, Citrobacter, Klebsiella, Proteus, Providencia, Morganella, Yersinia, Vibrio, Pseudomonas, Acinetobacter, Enterococcus, Staphylococcus, Streptococcus, Listeria, Bacillus, Candida, Cryptococcus, Saccharomyces*.

Accordingly, the invention relates to the use of a compound of the following formula (I) as enzyme substrate for the detection of a nitroreductase activity:

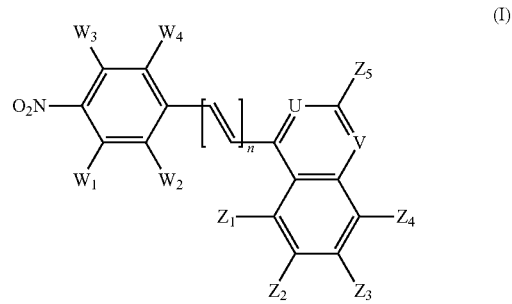

according to which:
- $W_1$, $W_2$, $W_3$ and $W_4$ are independently H, Br, Cl, F, I, alkyl, alkoxy, thiomethyl, perfluoroalkyl, nitro, cyano, carboxyl (including its esters or amides) or any combination thereof
- n=0, 1 or 2
- U is N or $N^+R$ and V is $CZ_6$ N or $N^+R$ or V is N or $N^+R$ and U is $CZ_6$, R being H, alkyl, aralkyl, aryl, alkanoic or alkylsulfonic
- $Z_1$, $Z_2$, $Z_3$, $Z_4$, $Z_5$ and $Z_6$ being independently H, Br, Cl, F, I, alkyl, aryl, alkoxy, perfluoroalkyl, nitro, cyano, carboxyl, sulfonyl, including the esters or amides of carboxyl or sulfonyl and salts thereof.

According to another embodiment of the invention, the latter relates to the use of a compound of formula (I) as indicated above, as enzyme substrate for the detection of a nitroreductase activity and indicator of a pH variation.

According to a preferred embodiment of the invention, n=1.

According to a preferred embodiment of the invention, U is N or $N^+R$ and V is $CZ_6$, preferably CH.

According to a preferred embodiment of the invention, V is N or $N^+R$ and U is $CZ_6$, preferably CH.

According to a preferred embodiment of the invention, $W_1$, $W_2$, $W_3$ and $W_4$ are independently H.

According to a preferred embodiment of the invention, $Z_1$, $Z_2$, $Z_3$, $Z_4$, $Z_5$ and $Z_6$ are H.

According to a preferred embodiment of the invention, said compound is chosen from: 2-(4'-nitrostyryl)quinoline (2NSQ), 2-(4'-nitrostyryl)-N-methylquinolinium iodide (2NSMQ$^+$I), 2-(4'-nitrophenyl)butadienyl-N-methylquinolinium iodide (2NPBMQ$^+$I), 4-(4'-nitrostyryl)-N-methyl-quinolinium iodide (4NSMQ$^+$I) and 4-(4'-nitro-2'-methoxystyryl)-N-methylquinolinium iodide (4NMSMQ$^+$I), 4-(4'-nitrophenyl)-2-methylquinoline, 2-(4'-nitrostyryl)-N-methylquinolinium TFA, 4-(4'-nitrostyryl)-N-benzylquinolinium TFA, 4-(4'-nitrostyryl)-N-methylquinolinium chloride, 4-(4'-nitrostyryl)quinaldinium hydrobromide, 4-(4'-nitrostyryl)quinaldinium methiodide, 4-(4'-nitrostyryl)quinoline TFA, 2-(2'-pyridyl)-4-(4''-nitrostyryl)quinoline, 4-(4'-nitrostyryl)-N-methylquinolinium TFA.

According to a preferred embodiment of the invention, said compound is chosen from 2-(4'-nitrostyryl)quinoline (2NSQ), 2-(4'-nitrostyryl)-N-methylquinolinium iodide (2NSMQ$^+$I), 2-(4'-nitrophenyl)butadienyl-N-methylquinolinium iodide (2NPBMQ$^+$I), 4-(4'-nitrostyryl)-N-methylquinolinium iodide (4NSMQ$^+$I) and 4-(4'-nitro-2'-methoxystyryl)-N-methylquinolinium iodide (4NMSMQ$^+$I).

The invention also relates to a method of detecting in microorganisms a nitroreductase activity, characterized in that it comprises the following steps:
a) having available a detection and/or identification medium comprising a compound of formula (I)

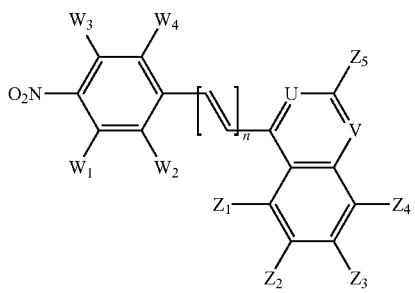

(I)

according to which:
$W_1$, $W_2$, $W_3$ and $W_4$ are independently H, Br, Cl, F, I, alkyl, alkoxy, thiomethyl, perfluoroalkyl, nitro, cyano, carboxyl (including its esters or amides) or any combination thereof
n=0, 1 or 2
U is N or N$^+$R and V is $CZ_6$ N or N$^+$R or V is N or N$^+$R and U is $CZ_6$, R being H, alkyl, aralkyl, aryl, alkanoic or alkylsulfonic
$Z_1$, $Z_2$, $Z_3$, $Z_4$, $Z_5$ and $Z_6$ being independently H, Br, Cl, F, I, alkyl, aryl, alkoxy, perfluoroalkyl, nitro, cyano, carboxyl, sulfonyl, including the esters or amides of carboxyl or sulfonyl
and salts thereof;
b) inoculating the medium with a biological sample to be tested,
c) allowing to incubate, and
d) detecting the presence of at least one nitroreductase activity.

According to another embodiment of the invention, the latter also relates to a method of detecting in microorganisms a nitroreductase activity and a pH variation, characterized in that it comprises the following steps:
a) having available a detection and/or identification medium comprising a compound of formula (I) as indicated above;
b) inoculating the medium with a biological sample to be tested;
c) allowing to incubate;
d) observing a change in the color and/or fluorescence of the detection and/or identification medium, detecting the presence of at least one nitroreductase activity, and a pH variation in said detection and/or identification medium.

According to a preferred embodiment of the invention, n=1.
According to a preferred embodiment of the invention, U is N or N$^+$R and V is $CZ_6$, preferably CH.
According to a preferred embodiment of the invention, V is N or N$^+$R and U is $CZ_6$, preferably CH.
According to a preferred embodiment of the invention, $W_1$, $W_2$, $W_3$ and $W_4$ are independently H.
According to a preferred embodiment of the invention, $Z_1$, $Z_2$, $Z_3$, $Z_4$, $Z_5$ and $Z_6$ are H.
According to a preferred embodiment of the invention, said compound is chosen from: 2-(4'-nitrostyryl)quinoline (2NSQ), 2-(4'-nitrostyryl)-N-methylquinolinium iodide (2NSMQ$^+$I), 2-(4'-nitrophenyl)butadienyl-N-methylquinolinium iodide (2NPBMQ$^+$I), 4-(4'-nitrostyryl)-N-methyl-quinolinium iodide (4NSMQ$^+$I) and 4-(4'-nitro-2'-methoxystyryl)-N-methylquinolinium iodide (4NMSMQ$^+$I), 4-(4'-nitrophenyl)-2-methylquinoline, 2-(4'-nitrostyryl)-N-methylquinolinium TFA, 4-(4'-nitrostyryl)-N-benzylquinolinium TFA, 4-(4'-nitrostyryl)-N-methylquinolinium chloride, 4-(4'-nitrostyryl)quinaldinium hydrobromide, 4-(4'-nitrostyryl)quinaldinium methiodide, 4-(4'-nitrostyryl)quinoline TFA, 2-(2'-pyridyl)-4-(4''-nitrostyryl)quinoline, 4-(4'-nitrostyryl)-N-methylquinolinium TFA.

According to a preferred embodiment of the invention, said compound is chosen from 2-(4'-nitrostyryl)quinoline (2NSQ), 2-(4'-nitrostyryl)-N-methylquinolinium iodide (2NSMQ$^+$I), 2-(4'-nitrophenyl)butadienyl-N-methylquinolinium iodide (2NPBMQ$^+$I), 4-(4'-nitrostyryl)-N-methylquinolinium iodide (4NSMQ$^+$I) and 4-(4'-nitro-2'-methoxystyryl)-N-methylquinolinium iodide (4NMSMQ$^+$I).

The inoculation of the microorganisms may be carried out by any inoculation techniques known to a person skilled in the art. An incubation step may be carried out at a temperature for which the enzyme activity which it is desired to detect is optimal, which a person skilled in the art can easily choose according to the enzyme activity to be detected. Step d) may be carried out by visual examination, by colorimetry or fluorometry. During step d), the presence of the nitroreductase activity may be detected, alone or in combination with at least one other enzyme activity.

The invention also relates to a medium for the detection and/or identification of microorganisms comprising a compound of the following formula (I):

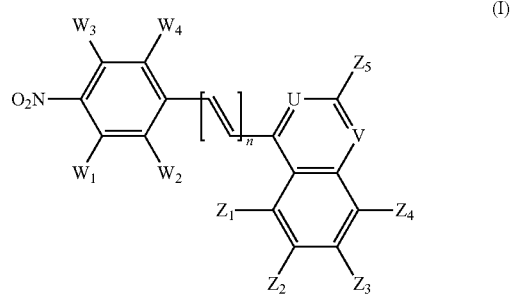

(I)

according to which:
$W_1$, $W_2$, $W_3$ and $W_4$ are independently H, Br, Cl, F, I, alkyl, alkoxy, thiomethyl, perfluoroalkyl, nitro, cyano, carboxyl (including its esters or amides) or any combination thereof n=0, 1 or 2

U is N or $N^+R$ and V is $CZ_6$ N or $N^+R$ or V is N or $N^+R$ and U is $CZ_6$, R being H, alkyl, aralkyl, aryl, alkanoic or alkylsulfonic $Z_1$, $Z_2$, $Z_3$, $Z_4$, $Z_5$ and $Z_6$ being independently H, Br, Cl, F, I, alkyl, aryl, alkoxy, perfluoroalkyl, nitro, cyano, carboxyl, sulfonyl, including the esters or amides of carboxyl or sulfonyl and salts thereof.

According to a preferred embodiment of the invention, n=1.

According to a preferred embodiment of the invention, U is N or $N^+R$ and V is $CZ_6$, preferably CH.

According to a preferred embodiment of the invention, V is N or $N^+R$ and U is $CZ_6$, preferably CH.

According to a preferred embodiment of the invention, $W_1$, $W_2$, $W_3$ and $W_4$ are independently H.

According to a preferred embodiment of the invention, $Z_1$, $Z_2$, $Z_3$, $Z_4$, $Z_5$ and $Z_6$ are H.

According to a preferred embodiment of the invention, said compound is chosen from: 2-(4'-nitrostyryl)quinoline (2NSQ), 2-(4'-nitrostyryl)-N-methylquinolinium iodide (2NSMQ$^+$I), 2-(4'-nitrophenyl)butadienyl-N-methylquinolinium iodide (2NPBMQ$^+$I), 4-(4'-nitrostyryl)-N-methyl-quinolinium iodide (4NSMQ$^+$I) and 4-(4'-nitro-2'-methoxystyryl)-N-methylquinolinium iodide (4NMSMQ$^+$I), 4-(4'-nitrophenyl)-2-methylquinoline, 2-(4'-nitrostyryl)-N-methylquinolinium TFA, 4-(4'-nitrostyryl)-N-benzylquinolinium TFA, 4-(4'-nitrostyryl)-N-methylquinolinium chloride, 4-(4'-nitrostyryl) quinaldinium hydrobromide, 4-(4'-nitrostyryl) quinaldinium methiodide, 4-(4'-nitrostyryl)quinoline TFA, 2-(2'-pyridyl)-4-(4''-nitrostyryl)quinoline, 4-(4'-nitrostyryl)-N-methylquinolinium TFA.

According to a preferred embodiment of the invention, said compound is chosen from 2-(4'-nitrostyryl)quinoline (2NSQ), 2-(4'-nitrostyryl)-N-methylquinolinium iodide (2NSMQ$^+$I), 2-(4'-nitrophenyl)butadienyl-N-methylquinolinium iodide (2NPBMQ$^+$I), 4-(4'-nitrostyryl)-N-methylquinolinium iodide (4NSMQ$^+$I) and 4-(4'-nitro-2'-methoxystyryl)-N-methylquinolinium iodide (4NMSMQ$^+$I).

Preferably, said reaction medium is a medium for the detection and/or identification of microorganisms, said medium comprising at least one molecule used as enzyme substrate as defined above.

Preferably, said compound is at a concentration of between 1 and 1000 mg/l, preferably between 10 and 500 mg/l.

Preferably, said reaction medium is a medium for the detection and/or identification of microorganisms, said medium additionally comprising at least one compound whose metabolism causes a pH variation. Preferably, said compound is a sugar, an amino acid or an organic acid. Preferably, said compound is a pentose, a hexose, a disaccharide, a trisaccharide or a polysaccharide.

Preferably, said compound is at a concentration of between 0.1 and 100 g/l, preferably between 1 and 50 g/l. Preferably, said compound is at a concentration of between 5 and 30 g/l.

According to a particular embodiment of the invention, said detection and/or identification medium according to the invention additionally comprises at least one other enzyme substrate, specific for an enzyme activity that is different from the nitroreductase activity detected by the molecule according to the invention.

The enzymatic metabolism of the other substrate(s) generates a detectable signal, different from the signal generated by the compound according to the invention used as enzyme substrate, such as for example different colored or fluorescent products, in order to allow visualization for the detection and/or the identification and/or the quantification of one or more microorganisms. By way of other specific substrates, it is possible to use any other substrate conventionally used in the detection of microorganisms. The concentration of the other specific enzyme substrate is generally between 0.01 and 1 g/l. Persons skilled in the art may be able to easily determine such a concentration according to the substrate used. As a guide, it is possible to combine the compounds according to the invention with peptidase, osidase, esterase or reductase enzyme substrates.

According to a particular embodiment of the invention, said detection and/or identification medium according to the invention additionally comprises at least one other enzyme substrate specific for the nitroreductase activity. Through the particular choice of substrates, it is then possible to identify groups of microorganisms expressing the same enzyme activity. The concentration of the other specific enzyme substrate is generally between 0.01 and 1 g/l. Persons skilled in the art may be able to easily determine such a concentration according to the substrate used.

According to a particular embodiment of the invention, said detection and/or identification medium according to the invention additionally comprises at least one metabolic indicator, specific for a metabolic activity different from that detected by the compound according to the invention.

This metabolic indicator may be in particular a Carbon or Nitrogen source associated or otherwise with a reagent detecting its metabolism.

The examples below are given by way of explanation and are not at all limiting. They make it possible to better understand the invention.

EXAMPLES

Example 1

Synthesis of Substrates 2-(4'-Nitrostyrylquinoline) was prepared according to the method of Skidmore and Tidd (S. Skidmore and E. Tidd, Journal of the Chemical Society, 1959, 1641-1645). Iodinated N-methyl-4-(4'-nitrostyrylquinolinium) was prepared from iodinated N-methyl-4-methylquinolinium according to the method of Bahner et al. (C. Bahner, J. Dale, J. Fain, E. Franklin, J. Goan, W. Stump, M. West and J. Wilson, Journal of Organic Chemistry, 1957, 22, 1110). Iodinated N-methyl-2-(4'-nitrostyrylquinolinium) was obtained according to a similar method [$^1$H-NMR ($d_6$-DMSO): δ 9.20 (1H, d, J=7 Hz, ArH), 8.62 (2H, m, ArH), 8.42-8.18 (9H, m, ArH and >CH=), 4.62 (3H, s, $NCH_3$)].

Other examples of typical substrates obtained in a manner similar to that mentioned above:

Iodinated N-methyl-4-(4'-nitro-2'-methoxystyrylquinolinium): this compound was prepared from iodinated N-methyl-4-methylquinolinium and 4-nitro-2-methoxy-benzaldehyde.

$^1$H-NMR (d$_6$-DMSO): δ 9.40 (1H, d, J 6 Hz, ArH), 8.88 (1H, d, J=8 Hz, ArH), 8.58-7.90 (9H, m, ArH and >CH=), 4.58 (3H, s, NCH$_3$), 4.08 (3H, s, —OCH$_3$).

Iodinated N-methyl-2-(4'-nitrophenyl-1,3-butadienyl)-quinolinium: this compound was prepared from iodinated N-methyl-2-methylquinolinium and 4-nitrocinnamaldehyde.

$^1$H-NMR (d$_6$-DMSO): δ 9.80 (1H, d, J=8 Hz, ArH), 8.52 (2H, m), 8.38-7.86 (8H, m, ArH and >CH=), 7.70 (2H, m >CH=), 7.35 (1H, d, J=18 Hz, >CH=), 4.50 (3H, s, NCH$_3$).

Example 2

Use of Substrates of Formula I According to the Invention to Detect a Nitroreductase Activity a) Nitroreductase Substrates The compounds 2-(4'-nitrostyryl)quinoline (2NSQ), 2-(4'-nitrostyryl)-N-methylquinolinium iodide (2NSMQ$^+$I), 2-(4'-nitrophenyl)butadienyl-N-methylquinolinium iodide (2NPBMQ$^+$I), 4-(4'-nitrostyryl)-N-methylquinolinium iodide (4NSMQ$^+$I) and 4-(4'-nitro-2'-methoxystyryl)-N-methylquinolinium iodide (4NMSMQ$^+$I) were synthesized as described in example 1.

b) Preparation of the Medium 40 mg of each of the substrates were dissolved in 4 ml of dimethylsulfoxide and added to 400 ml of previously autoclaved Columbia medium. The 5 media were distributed in Petri dishes 90 mm in diameter at the rate of 20 ml per dish.

c) Inoculation and Incubation

Seventeen strains of microorganisms obtained from collections and belonging to various species of bacteria and yeasts are inoculated as spots of about 10 000 colony forming units.

The media are incubated for 24 hours at 37° C. and then the colonies formed are examined visually and under a UV lamp at 365 nm.

d) Reading of the Results

The results obtained are presented in table 1.

TABLE 1

Color of the colonies in the presence of nitro-reductase substrates according to the invention

| Species | 2NSQ | | | 2NSMQ$^+$I | | 2NPBMQ$^+$I | | 4NSMQ$^+$I | | | 4NMSMQ$^+$I | | |
| --- | --- | --- | --- | --- | --- | --- | --- | --- | --- | --- | --- | --- | --- |
| Collection number | Growth | Col. | Fluo. | Growth | Col. | Growth | Col. | Growth | Col. | Fluo. | Growth | Col. | Fluo. |
| Escherichia coli NCTC 10 418 | 2 | — | Pale blue | 2 | Dark rust | 2 | Dark rust | 2 | Dark rust | Pale blue | 2 | Pale orange | Pale yellow |
| Serratia marcescens NCTC 10 211 | 2 | — | Pale blue | 2 | Dark rust | 2 | Dark rust | 2 | Dark rust | Pale blue | 2 | Pale orange | Pale yellow |
| Pseudomonas aeruginosa NCTC 10 662 | 2 | — | — | 2 | Dark rust | 2 | Orange | 2 | Dark rust | — | 1 | — | — |
| Yersinia enterocolitica NCTC 11 176 | 2 | — | — | 2 | Rust | 1 | Pale orange | 1 | Rust | — | 2 | — | — |
| Salmonella typhimurium NCTC 74 | 2 | — | — | 2 | Pale rust | 1 | Pale orange | 1 | Marron pâle | — | 1 | — | — |
| Enterobacter cloacae NCTC 11 936 | 2 | — | Pale blue | 2 | Dark rust | 2 | Orange | 2 | Rust | Pale blue | 2 | Pale orange | Pale yellow |
| Providencia rettgeri NCTC 7 475 | 2 | — | — | 2 | Rust | 2 | Orange | 2 | Rust e | — | 0.5 | — | — |
| Bacillus subtilis NCTC 9 372 | 1 | — | — | 1 | Pale rust | 0.5 | — | NG | — | — | 2 | Pale orange | — |
| Enterococcus faecalis NCTC 775 | 1 | — | — | 1 | Pale rust | 1 | Pale orange | 1 | Rust | — | 2 | Pale orange | — |
| Enterococcus faecium NCTC 7 171 | 1 | — | — | 1 | Pale rust | 1 | Pale orange | 1 | Rust | — | 0.5 | — | — |
| Staphylococcus epidermidis NCTC 11 047 | 1 | — | — | 0.5 | — | 1 | — | 1 | — | — | 2 | Pale orange | — |
| Staphylococcus aureus NCTC 6 571 | 1 | — | — | NG | — | NG | — | NG | — | — | 2 | Pale orange | — |
| Staphylococcus aureus NCTC 11 939 | 1 | — | — | NG | — | NG | — | NG | — | — | 2 | Pale orange | — |
| Streptococcus pyogenes NCTC 8 306 | 1 | — | — | 0.5 | Pale rust | 0.5 | — | NG | — | — | 1 | — | — |
| Listeria monocytogenes NCTC 11 994 | 1 | — | — | 1 | Pale rust | 1 | Pale orange | 1 | Rust | — | 2 | — | — |
| Candida albicans ATCC 90 028 | 0.5 | — | — | 0.5 | — | NG | — | NG | — | — | 0.5 | — | — |
| Candida glabrata NCPF 3 943 | 1 | — | — | NG | — | NG | — | 0.5 | — | — | NG | — | — |

Fluo.: fluorescence of the colonies,
Col.: color of the colonies,
NG: no growth,
0.5: low growth,
1: moderate growth,
2: good growth,
—: no color/fluorescence e) Conclusions On the media according to the invention, it is possible to detect a nitroreductase activity of microorganisms with the aid of the fluorescence or the color of the colonies.

Most often, the substrates, according to the invention allow the growth of any type of microorganism: Gram-negative bacteria, Gram-positive bacteria, yeasts and the like.

Using different variations of the structure of the nitroreductase substrates according to the invention, it is possible to distinguish various groups of microorganisms and to obtain various colors of colonies. Furthermore, since the color does not diffuse in the reaction medium, it is possible to distinguish and count the cells or colonies expressing the nitroreductase activity independently of those not expressing it.

The invention claimed is:

1. A method for detecting in microorganisms a nitroreductase activity, comprising the following steps:
   a) having available a detection and/or identification medium comprising a compound of formula (I)

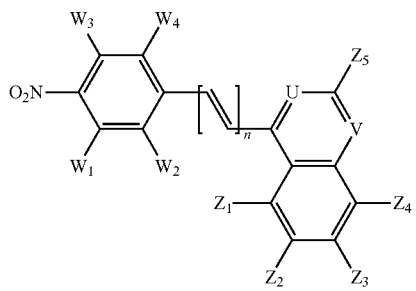

(I)

wherein:
   $W_1$, $W_2$, $W_3$ and $W_4$ are independently H, Br, Cl, F, I, alkyl, alkoxy, thiomethyl, perfluoroalkyl, nitro, cyano, carboxyl, carboxyl esters or carboxyl amides or any combination thereof n=0, 1 or 2
   wherein if U is N or $N^+R$ and then V is $CZ_6$ or N, R being H, alkyl, aralkyl, aryl, alkanoic or alkylsulfonic
   $Z_1$, $Z_2$, $Z_3$, $Z_4$, $Z_5$ and $Z_6$ being independently H, Br, Cl, F, I, alkyl, aryl, alkoxy, perfluoroalkyl, nitro, cyano, carboxyl, sulfonyl, including the esters or amides of carboxyl or sulfonyl
and salts thereof;
   b) inoculating the medium with a biological sample to be tested,
   c) allowing to incubate, and
   d) detecting the presence of at least one nitroreductase activity.

2. The method of claim 1, wherein the compound of formula (I) also detects a variation in pH.

3. The method of claim 1, wherein n=1.

4. The method of claim 1, wherein $W_1$, $W_2$, $W_3$ and $W_4$ are independently H.

5. The method of claim 1, wherein U is N or $N^+R$ and V is $CZ_6$.

6. The method of claim 1, wherein $Z_1$, $Z_2$, $Z_3$, $Z_4$, $Z_5$ and $Z_6$ are H.

7. The method of claim 1 wherein said compound is chosen from: 2-(4'-nitrostyryl)quinoline (2NSQ), 2-(4'-nitrostyryl)-N-methylquinolinium iodide ($2NSMQ^+I$), 2-(4'-nitrophenyl)butadienyl-N-methylquinolinium iodide ($2NPBMQ^+I$), 4-(4'-nitrostyryl)-N-methyl-quinolinium iodide ($4NSMQ^+I$) and 4-(4'-nitro-2'-methoxystyryl)-N-methylquinolinium iodide ($4NMSMQ^+I$), 4-(4'-nitrophenyl)-2-methylquinoline, 2-(4'-nitrostyryl)-N-methylquinolinium TFA, 4-(4'-nitrostyryl)-N-benzylquinolinium TFA, 4-(4'-nitrostyryl)-N-methylquinolinium chloride, 4-(4'-nitrostyryl)quinaldinium hydrobromide, 4-(4'-nitrostyryl)quinaldinium methiodide, 4-(4'-nitrostyryl)quinoline TFA, 2-(2'-pyridyl)-4-(4"-nitrostyryl)quinoline, 4-(4'-nitrostyryl)-N-methylquinolinium TFA.

* * * * *